United States Patent [19]

Pinkerton

[11] 4,178,240
[45] Dec. 11, 1979

[54] FLUID HANDLING SYSTEM

[76] Inventor: Harry E. Pinkerton, Bridle Path La., Mill Neck, N.Y. 11765

[21] Appl. No.: 686,856

[22] Filed: May 17, 1976

[51] Int. Cl.$^2$ .................... B01D 31/00; B01D 13/00
[52] U.S. Cl. .................... 210/22 A; 128/214 E; 137/99; 417/393; 417/395; 417/404; 210/321 B
[58] Field of Search ............ 137/99; 210/22, 321 B, 210/321 A; 417/393, 395, 404; 128/214 R, 214 E

[56] References Cited

U.S. PATENT DOCUMENTS

| | | | |
|---|---|---|---|
| 3,530,873 | 9/1970 | Arp et al. | 137/99 |
| 3,791,768 | 2/1974 | Wanner | 137/99 X |
| 3,976,574 | 8/1976 | White | 210/321 A X |
| 3,979,284 | 9/1976 | Granger et al. | 210/22 A |
| 4,021,341 | 5/1977 | Cosentino et al. | 210/103 X |
| 4,093,545 | 6/1978 | Cullis | 210/86 |

OTHER PUBLICATIONS

McDonald, Jr., "An Automatic Peritoneal Dialysis Machine for Hospital or Home Peritoneal Dialysis: Preliminary Report," from vol. XV, Trans. Amer. Soc. Artif. Int. Organs, 1969, pp. 108–113.

Primary Examiner—Frank A. Spear, Jr.
Attorney, Agent, or Firm—A. C. Nolte, Jr.; Edward B. Hunter

[57] ABSTRACT

A system for handling two liquid streams comprises an hydraulic circuit including a pair of receptacles each provided with movable partition means dividing it into first and second chambers. Rod means extending through a first chamber of each receptacle connects the partition means and is effective to cause reciprocation of one partition means to be repeated by the other so that as the first chamber of one receptacle is expanded, the first chamber of the other receptacle is contracted. A quantity of the first liquid is delivered alternately to the first and second chambers of one receptacle as those chambers expand. As those chambers contract first liquid is passed through conduit means from the first and second chambers of said one receptacle to the first and second chambers, respectively, of said other receptacle. A source of second liquid is connected to said conduit means and liquid removal means is connected to said circuit to remove liquid from said circuit in quantities equal to the quantity of second liquid admitted to the circuit.

16 Claims, 3 Drawing Figures

FLUID HANDLING SYSTEM

BACKGROUND OF THE INVENTION

This invention is concerned with fluid handling systems, such as, for example, reverse osmosis and hemodialysis systems in which it is required to monitor and control the flow rates of each of two merging fluid streams, a main stream and a secondary stream. In application, Ser. No. 590,897 filed June 25, 1975 and now abandoned in favor of application Ser. No. 687,133 filed May 17, 1976, there is described a system for handling two liquid streams which essentially consists in delivering volume of the first liquid to a chamber to fill that chamber, making a connection from that chamber a second and larger chamber and passing said determined volume of first liquid from the first chamber to the second chamber through said connection, a connection being made between a supply of second liquid and said connection between the two chambers so that the second liquid is induced into the second chamber in an amount equal to the difference in volumes between said chambers.

When that system is applied in a hemodialysis procedure, the source of second liquid is the dialysis cell and the second liquid comprises blood wastes, the blood wastes being drawn across the membrane of the cell by the negative pressure induced by the passage of the first liquid to the chamber of greater volume, the blood wastes being pulled across the cell in quantities equal to the difference in volumes of the two chambers.

In co-pending application Ser. No. 645,747 filed Dec. 31, 1975 there is described and illustrated another fluid handling system which comprises an hydraulic circuit with, in its simplest form, a receptacle, movable partition dividing the receptacle into first and second chambers, that partition being reciprocated within the receptacle to displace equal volumes in the two chambers. A conduit connects the two chambers and a source of a second liquid is connected to that conduit. In operation, first liquid is admitted to one chamber as that chamber expands and as that chamber contracts through reciprocation of the partition, that first liquid is passed through the conduit to the second chamber. Means are provided for removing liquid from the circuit so that second liquid is induced into the circuit in quantities equal to the amount of liquid removed through said liquid removal means.

The liquid removal means may consist of a simple outlet when the device is used in a dialysis system in which case liquid will pass through the outlet in quantities directly related to the quantity of blood waste migrating across the membrane of the cell or there may be provided a pump unit for removing predetermined quantities of liquid. Reference is made to said co-pending applications for a more detailed description of the inventions thereof.

The present invention is concerned with fluid handling systems of these general kinds.

BRIEF SUMMARY OF THE INVENTION

The present invention seeks to provide apparatus for and a method of handling liquids in which the flow of a second liquid from an isolated source into a main liquid stream can be accurately measured and controlled without direct contact with the secondary liquid.

According to the invention, there is provided an hydraulic circuit comprising a pair of receptacles each divided by ganged, reciprocable partition means into first and second chambers, reciprocation of said partition means causing first equal volumes to be swept in each said first chambers and second equal volumes to be swept in each said second chambers. Determined volumes of first liquid are alternately delivered to the chambers of one receptacle as those chambers expand and are transferred, through conduit means, to equal volume chambers of said second receptacle as said chambers contract. A second liquid connection is made to said conduit means and fluid removal means are provided for removing portions of said volumes from said circuit to cause second liquid to be introduced into said conduit means in quantities equal to said removed portions.

The volumes of said first chambers may be the same as said volumes of said second chambers or they may be different

BRIEF DESCRIPTION OF THE FIGURES OF THE DRAWINGS

Embodiments of this invention are illustrated, schematically, in the accompanying drawings, in which.

DESCRIPTION OF THE PREFERRED EMBODIMENTS OF THE INVENTION

Figure 1:
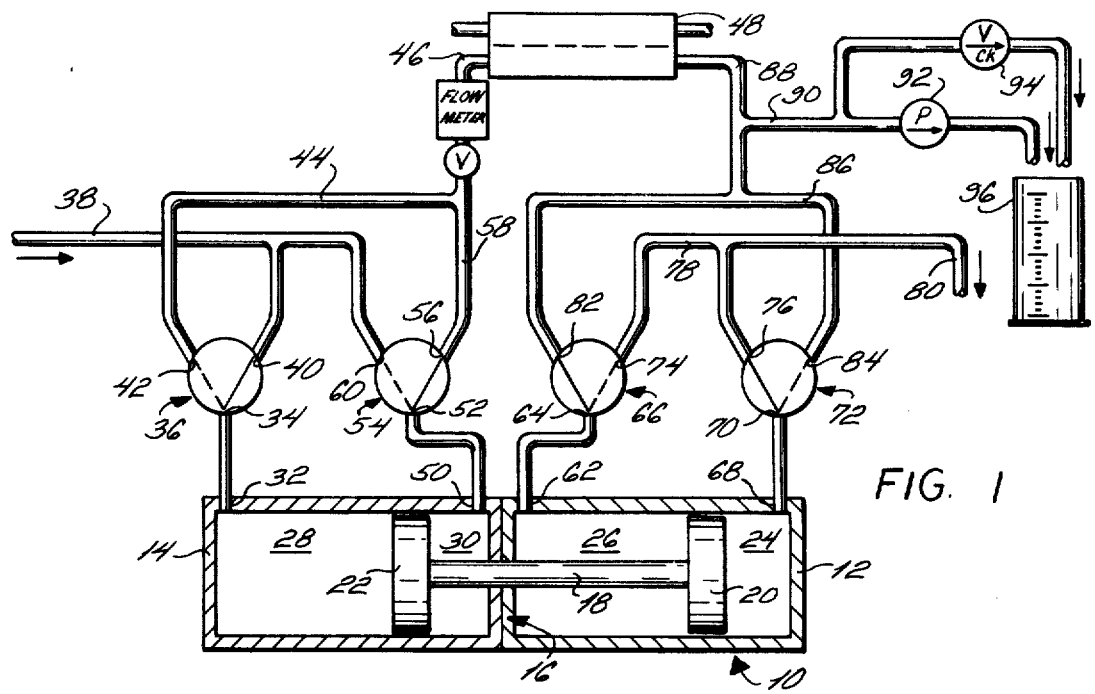
FIG. 1 shows one embodiment of the present invention.

The embodiment of the invention in FIG. 1 comprises a cylinder structure, indicated generally at 10, comprising end walls 12 and 14 and a central wall 16 which divides the structure into two cylinders, one to either side of the central wall 16. Disposed for sliding movement in the central wall 16 is a rod 18 which at one end has a piston 20 and at its other a piston 22. The pistons 20 and 22 constituted the partition means discussed supra, the piston 20 dividing the right hand cylinder into two chambers 24 and 26, and piston 22 dividing the left hand cylinder into chambers 28 and 30.

A cylinder port 32 opens to chamber 28 and is connected to port 34 of a three port, two position valve 36. An inlet conduit 38 for the delivery of, in this case, dialysate solution which constitutes the first liquid, is connected to port 40 of valve 36. From port 42 of valve 36 conduit 44 leads to conduit 46 then to the solution side of dialysis cell 48.

Cylinder port 50 leads from chamber 30 to port 52 of a three port, two position valve 54 from port 56 of which, conduit 58 leads to conduit 46 which, as will be apparent, constitutes a common section of the connection between chambers 28 and 30 and the dialysis cell 48.

Dialysate solution inlet line 38 is connected to port 60 of valve 54.

Cylinder port 62 leads to port 64 of three port two position valve 66 and cylinder port 68 leads to port 70 of three port two position valve 72. Ports 74 and 76 of valves 66 and 72, respectively, are interconnected by conduit 78 which leads to a discharge conduit 80 and ports 82 and 84 of valves 66 and 72 are connected by conduit 86 while conduit 88 connects the solution side of cell 48 to conduit 86.

From conduit 88 a branch 90 leads to a metering pump 92 and a pump by-pass check valve 94, liquid passing pump 92 and valve 94 being delivered to a graduated vessel 96.

The operation of the apparatus of FIG. 1 is as follows:

With the valves in the positions shown in full line, dialysate solution is admitted through ports 40 and 34 to chamber 28 as the pistons 20 and 22 move left to right. Liquid in chamber 30, which, as will be described hereinafter, is also dialysate solution, passes through ports 52 and 56 of valve 54 and through conduits 58 and 46 to the cell 48. From the cell, liquid displaced from chamber 30 and blood wastes migrating across the membrane of the cell pass to conduit 88, then through ports 82 and 64 of valve 66 to chamber 26. In the meantime, liquid in chamber 24, which is a mixture of dialysis solution and blood wastes, as described hereinafter, passes, via ports 70 and 76 of valve 72, to discharge at 80.

Upon completion of left to right movement of the pistons, the valves are shifted from the position shown in full line to the position shown in chain line by any appropriate means, as for example limit switches, proximity switches, or by pressure responsive switches, those switches responding to pressure build-up as the pistons reach the limits of their movement. At this time, dialysate solution is admitted through ports 60 and 52 of valve 54 to chamber 30. The dialysate solution previously admitted to chamber 28 is now moved through ports 34 and 42 of valve 36 along conduit 44 to conduit 46 and then to cell 48. From the cell solution and blood wastes pass along conduit 88 and, via ports 84 and 70 of valve 72, to chamber 24. At the same time, the mixture of the solution and the blood wastes previously admitted to chamber 26 is removed from that chamber through ports 64 and 74 of valve 66 to waste at 80.

If the pump is set to extract no fluid from conduit 88, then the osmotic migration of blood wastes crossing the cell membrane will cause an excess pressure in line 90 since the connected chambers of the two cylinders are of equal volume. That excess pressure will cause one-way check valve 94 to be opened and a quantity of liquid to pass that valve to be captured in graduated vessel 96 for measuring. Similarly, if the pump 92 is set to extract liquid at a lesser rate than that at which the blood wastes migrate across the membrane of the cell the valve will also open so that the pump will deliver to vessel 96 that amount of liquid which it extracts and an excess, representing the additional quantity of blood wastes being extracted will pass check valve 94. In the event that the extraction rate set by pump 92 exceeds the osmotic migration of blood wastes across the cell, negative pressure filtration will occur, then valve 94 will remain closed and all the extracted liquid will be passed by pump 92 to vessel 96. In any event, the liquid which is delivered to vessel 96 is directly representative of the quantity of blood wastes drawn across the membrane of the cell.

Figure 2:
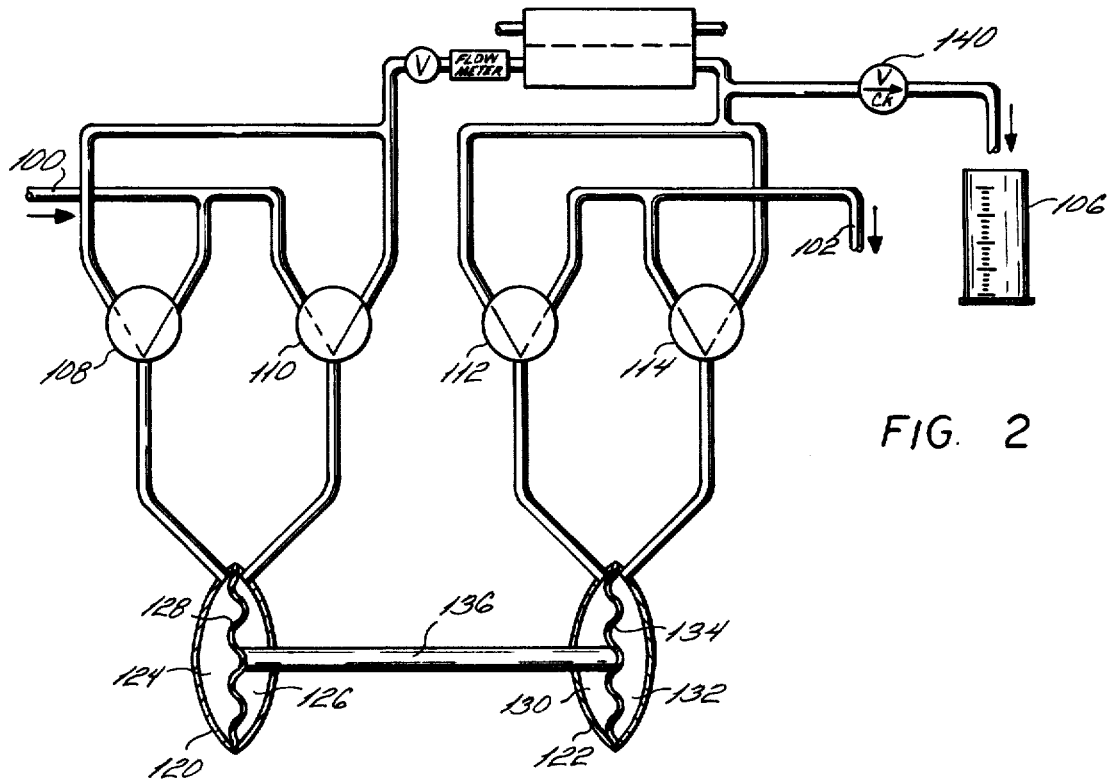
FIG. 2 shows an alternative embodiment.

The apparatus illustrated in FIG. 2 is in many respects similar to that of FIG. 1 and for this reason is not described in detail herein. Essentially, it comprises a dialysate inlet 100, a discharge 102, a graduated vessel 106 and valves 108, 110, 112 and 114 which serve the same roles as valves 36, 54, 66 and 72, respectively, of the embodiment of FIG. 1.

However, instead of the piston and cylinder structure, there are in the embodiment of FIG. 2 simple receptacles 120 and 122. Receptacle 120 is divided into two chambers 124 and 126 by a flexible diaphragm 128. Similarly, receptacle 122 is divided into chambers 130 and 132 by flexible diaphragm 134 and diaphragm 134 is ganged to diaphragm 128 by a rod 136 mounted for sliding movement in adjacent walls of receptacle 120 and 122.

The operation of the device of FIG. 2 is largely similar to that of FIG. 1. In the embodiment of FIG. 2, however, there is no pump and the check valve 140 simply provides for the venting of excess liquid drawn across the cell, to measuring chamber 106.

Figure 3:
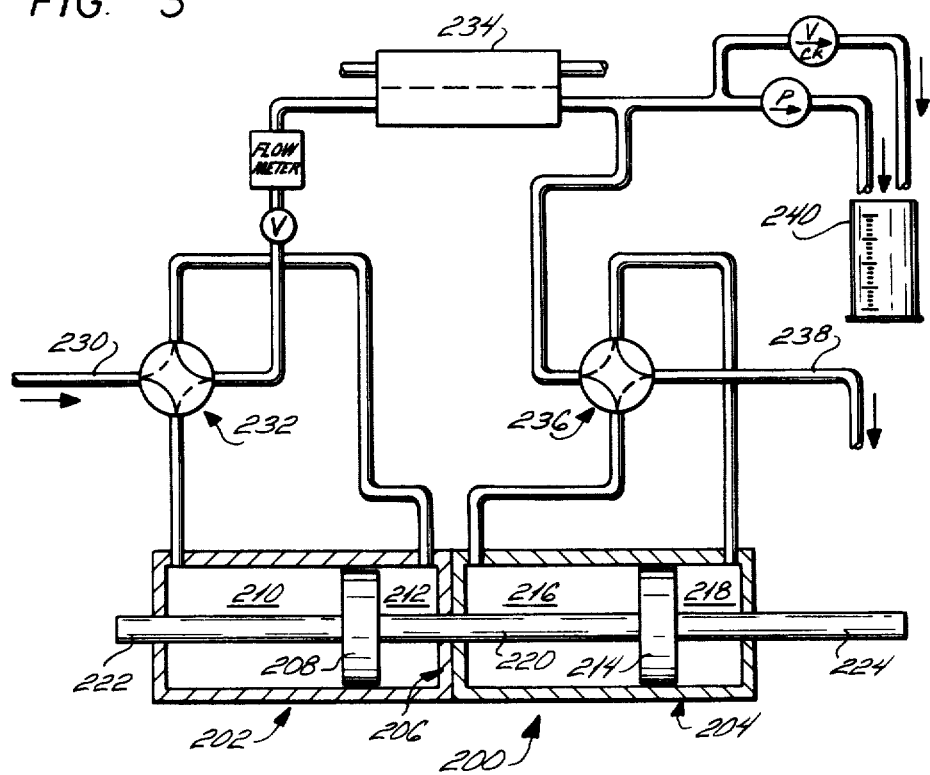
FIG. 3 shows a further embodiment.

The embodiment of the invention illustrated in FIG. 3 comprises a cylinder structure indicated generally at 200 defining two cylinders 202 and 204 separated by a central wall structure 206. Disposed within chamber 202 is a piston 208 which divides the cylinder into chambers 210 and 212 and similarly piston 214 is disposed in cylinder 204 and divides that cylinder into chambers 216 and 218. Ganging the two pistons together is a piston rod 220 and idler piston rod 222 extends from piston 208 to the exterior of cylinder 202 with a similar idler piston rod 224 extending from the right of piston 214 to the exterior of cylinder 204. Rods 220, 222 and 224 are of similar cross section so that reciprocation of pistons 208 and 214 within cylinders 202 and 204 causes the piston to sweep equal volumes in each of chambers 210, 212, 216 and 218.

A supply of dialysate solution is connected by conduit 230 and through four port valve 232 alternately to chambers 210 and 212 as those chambers expand during reciprocation of the pistons. As those chambers contract they are alternately connected through dialyzer cell 234 and four port valve 236 to chambers 218 and 216, respectively.

As chambers 216 and 218 are contracted they are connected through valve 236 to waste at 238.

As in the embodiments of FIGS. 1 and 2 a flow meter and a rate controlling valve V are provided in the connections between the chambers. Additionally, and as in the embodiment of FIG. 1, a pump and check valve are provided controlling outlets to a graduated measuring vessel 240.

It will be appreciated that the apparatus of this application is in many respects physically similar to that of the aforementioned application Ser. No. 687,133 and that the apparatus is arranged to operate on the principle of the equipment described in application Ser. No. 645,747, thus it is to be recognized that the invention is subject to the appropriate ones of the various modifications described in the aforementioned applications without deviating from its scope. Additionally, it will be appreciated that while the embodiments illustrated show the invention as applied to a dialysis system and particularly to the blood extraction part of such a system, the invention will find application in other fields. Further, when the device is used in a dialysis system, it will be recognized that other ancillary and conventional equipment will be used with it, as for example conventional heaters and de-gassers.

What is claimed is:

1. Apparatus for handling two liquids comprising a filled hydraulic system having a first receptacle and a second receptacle, reciprocable partition means in each of said receptacles dividing each receptacle into a first chamber and a second chamber, means causing reciprocation of said partition means alternately to expand and to contract said chambers, means ganging said partition means, means delivering first liquid to said chambers of said one receptacle alternately as each said chamber expands, conduit means transferring said first liquid to a chamber of equal volume in said second receptacle as each said chamber of said first receptacle contracts, inlet means for a second liquid in said conduit means and liquid removal means removing liquid from said system in quantities equal to the quantity of said second liquid admitted to said system.

2. Apparatus as claimed in claim 1 wherein said means ganging said partition means comprises rod means.

3. Apparatus as claimed in claim 1 wherein said receptacles comprise cylinders and said partition means comprise a piston in each cylinder.

4. Apparatus as claimed in claim 3 wherein said cylinders are disposed in end to end coaxial relationship and said means ganging said pistons comprises a common piston rod.

5. Apparatus as claimed in claim 1 wherein said reciprocable partition means comprises flexible diaphragm means.

6. Apparatus as claimed in claim 5 wherein said flexible diaphragm means are connected by a rod extending through first chambers of each said receptacle.

7. Apparatus as claimed in claim 1 wherein the volumes swept in said first chambers equal the volumes swept in said second chambers.

8. Apparatus as claimed in claim 1 wherein said inlet means for a second liquid is constituted by a membrane of a dialyzer cell.

9. Apparatus as claimed in claim 8 wherein said fluid removal means comprises an outlet opening from said conduit means.

10. Apparatus as claimed in claim 9 wherein said outlet opening is controlled by a check valve.

11. Apparatus as claimed in claim 9 wherein said removal means includes a metering pump.

12. Apparatus as claimed in claim 10 wherein said removal means includes a metering pump.

13. Apparatus as claimed in claim 1 wherein said removal means comprises a metering pump.

14. A method of handling liquids in an hydraulic system comprising a first receptacle and a second receptacle, partition means in each receptacle dividing the receptacles into first and second chambers, which method comprises reciprocating said partition means in said receptacles to cause, during reciprocation of said partition means, equal volumes of each first chamber to be swept by said partition means and equal volumes of each second chamber to be swept by said partition means, admitting first liquid alternately to each chamber of said first receptacle as it expands, transferring said first liquid from each said chamber of said first receptacle as it contracts, alternately to an expanding chamber of equal volume in said second receptacle, establishing a second liquid connection to said system and extracting from said system a quantity of said transferred liquid to induce quantities of said second liquid, equal to said extracted quantities, to be admitted to said expanding chamber of said second receptacle.

15. The method as claimed in claim 14 wherein volumes of said second chamber equal to volumes in said first chambers are caused to be swept.

16. A hemodialysis procedure utilizing a hydraulic system comprising a first and a second receptacle, and partition means in each receptacle dividing the receptacles into first and second chambers which procedure comprises connecting a patient to the blood side of a dialysis cell having blood and dialysate solution sides, reciprocating said partition means in said receptacles to cause, during reciprocation of said partition means, equal volumes of each first chamber to be swept by said partition means and equal volumes of each second chamber to be swept by said partition means, admitting a dialysate solution alternately to each chamber of said first receptacle as it expands, transferring said solution through the dialysate side of the dialysis cell from each said chamber of said first receptacle as it contracts, alternately to an expanding chamber of equal volume in said second receptacle whereby blood wastes migrate across the membrane from the blood side to the dialysate side of said cell, providing an outlet from said circuit whereby the egress of liquid from the circuit in direct volumetric relationship to the quantity of blood wastes crossing said membrane will occur through said outlet, and measuring that egress.

* * * * *